(12) United States Patent
Oyola et al.

(10) Patent No.: US 10,881,383 B2
(45) Date of Patent: Jan. 5, 2021

(54) SYSTEMS AND METHODS FOR HOMING AN AUTOMATED BIOPSY DRIVER FOR INSTALLING A DISPOSABLE BIOPSY NEEDLE ASSEMBLY

(71) Applicant: HOLOGIC, INC., Marlborough, MA (US)

(72) Inventors: Arnold Oyola, Northborough, MA (US); Joseph A. Stand, III, Holden, MA (US); Christian Michael Ulm, Ashland, MA (US); Debra Sue Pare, Newburyport, MA (US); David Anthony Gilstrap, Indianapolis, IN (US); Rangarajan Krishnamurthi, Ashland, MA (US); Thomas Fisk, Newton, MA (US)

(73) Assignee: Hologic, Inc., Marlborough, MA (US)

( * ) Notice: Subject to any disclaimer, the term of this patent is extended or adjusted under 35 U.S.C. 154(b) by 336 days.

(21) Appl. No.: 16/115,965

(22) Filed: Aug. 29, 2018

(65) Prior Publication Data

US 2019/0059865 A1    Feb. 28, 2019

Related U.S. Application Data

(60) Provisional application No. 62/553,033, filed on Aug. 31, 2017.

(51) Int. Cl.
| | |
|---|---|
| *A61B 5/00* | (2006.01) |
| *A61B 10/02* | (2006.01) |
| *A61B 10/00* | (2006.01) |
| *A61B 6/00* | (2006.01) |

(52) U.S. Cl.
CPC ...... *A61B 10/0283* (2013.01); *A61B 10/0096* (2013.01); *A61B 10/0275* (2013.01); *A61B 6/4405* (2013.01); *A61B 2010/0208* (2013.01)

(58) Field of Classification Search
CPC . A61B 10/02; A61B 10/0233; A61B 10/0275; A61B 10/0283; A61B 10/0096; A61B 2010/0208
See application file for complete search history.

(56) References Cited

U.S. PATENT DOCUMENTS

| | | | | |
|---|---|---|---|---|
| 8,852,121 B2 * | 10/2014 | Stephens | ............ | A61B 10/0275 600/567 |
| 9,101,351 B2 * | 8/2015 | Thompson | ......... | A61B 10/0275 |
| 9,433,402 B2 * | 9/2016 | Privitera | ............ | A61B 10/0266 |

(Continued)

*Primary Examiner* — Max F Hindenburg
(74) *Attorney, Agent, or Firm* — Vista IP Law Group, LLP

(57) ABSTRACT

A biopsy system includes a motorized driver having a drive member operatively coupled with a needle interface of a biopsy needle assembly that is removably installed on the motorized driver, wherein the motorized driver actuates the drive member to thereby actuate the biopsy needle assembly via the needle interface. A system controller that controls operation of the motorized driver is configured to perform a homing process including determining a system test failure or a needle removal condition in which a biopsy needle assembly installed on the motorized driver has been or should be removed from the motorized driver. Upon determining a system test failure or needle removal condition, the controller positions the drive member in a drive member home position for receiving a new biopsy needle assembly to be installed on the motorized driver.

20 Claims, 8 Drawing Sheets

(56) References Cited

U.S. PATENT DOCUMENTS

| | | |
|---|---|---|
| 9,492,130 B2 | 11/2016 | Flagle et al. |
| 2002/0111634 A1* | 8/2002 | Stoianovici ............ A61B 90/50 |
| | | 606/129 |
| 2010/0036245 A1* | 2/2010 | Yu ........................ A61N 5/1027 |
| | | 600/439 |
| 2010/0160815 A1* | 6/2010 | Parihar .............. A61B 10/0275 |
| | | 600/564 |
| 2016/0089121 A1 | 3/2016 | Stand et al. |

* cited by examiner

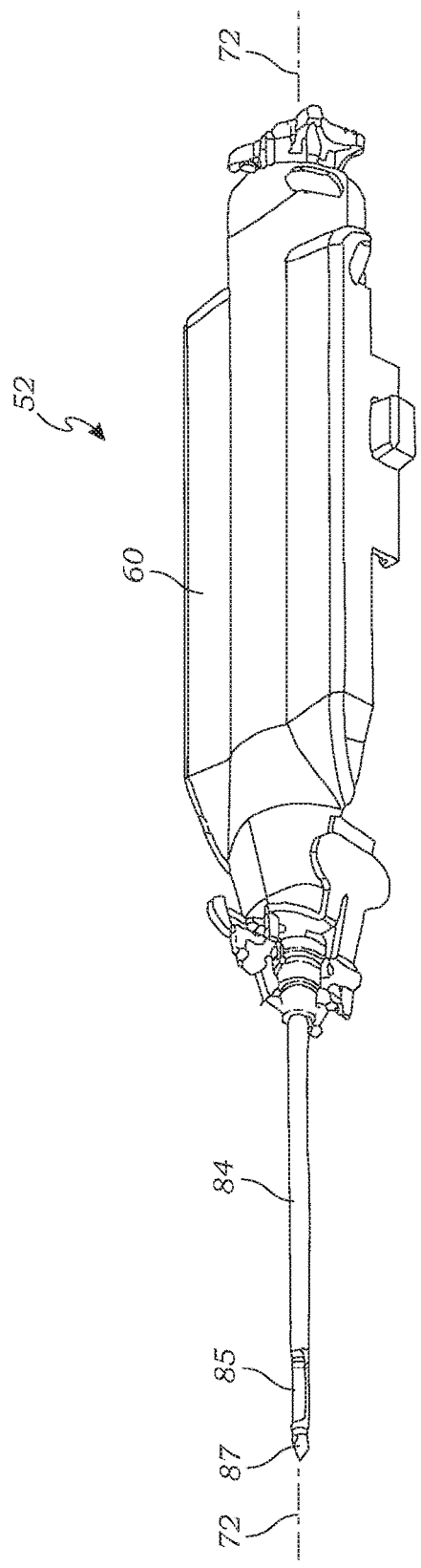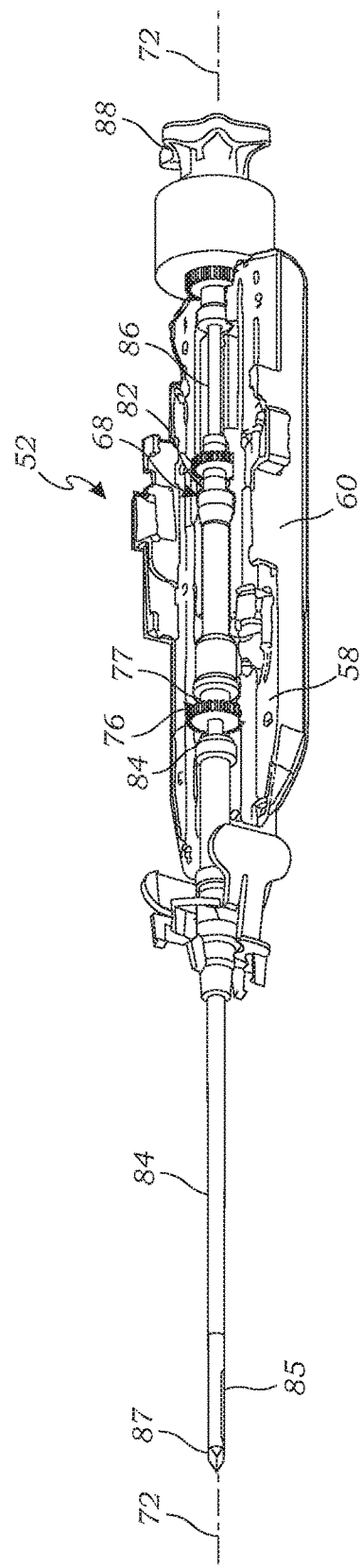
Fig. 4
Fig. 5

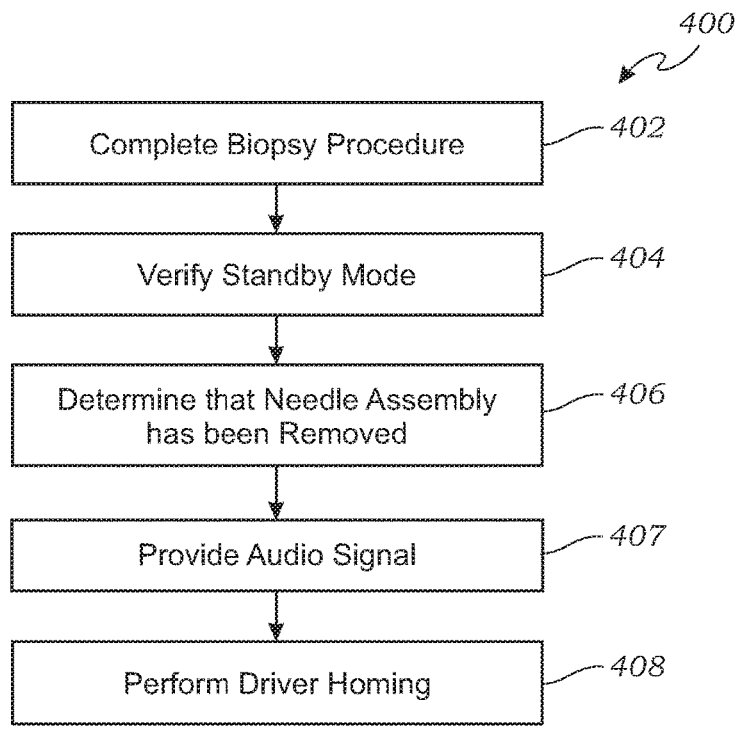
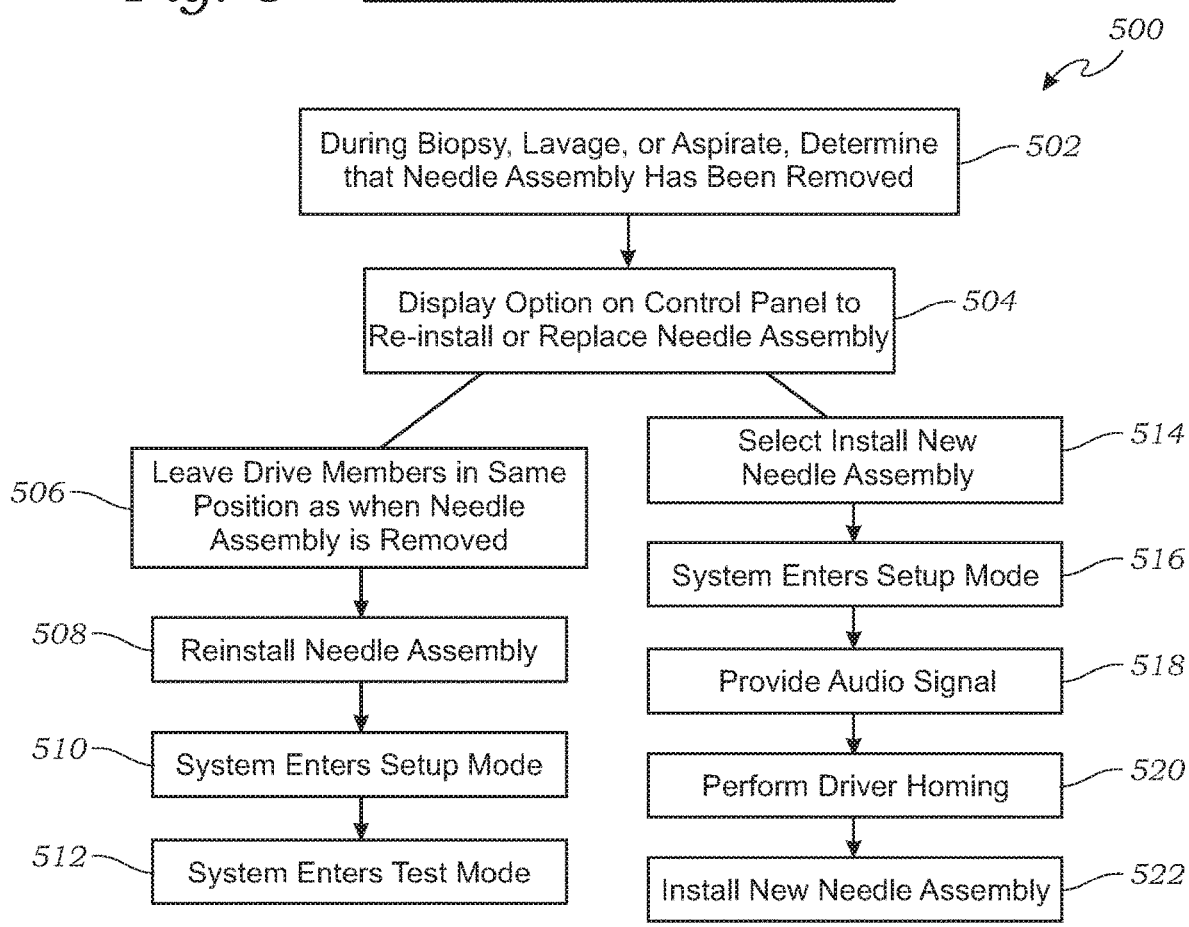

SYSTEMS AND METHODS FOR HOMING AN AUTOMATED BIOPSY DRIVER FOR INSTALLING A DISPOSABLE BIOPSY NEEDLE ASSEMBLY

RELATED APPLICATION DATA

The present application claims the benefit under 35 U.S.C. § 119 to U.S. provisional patent application Ser. No. 62/553,033, filed Aug. 31, 2017. The foregoing application is hereby incorporated by reference into the present application in its entirety.

FIELD

The disclosed inventions generally relate to automated systems and methods for preparation of biopsy tissue specimens for imaging, and more particularly, to systems and methods for homing an automated biopsy driver for installing a disposable biopsy needle assembly onto the driver.

BACKGROUND

Biopsies are well-known medical procedures involving the removal of tissue form a living body and examining the tissue for diagnostic study, such as determining the presence, cause or extent of a disease. For example, a biopsy of human breast tissue may be performed for diagnosing breast cancer or other diseases. In general, a biopsy can be performed by either an open procedure or a percutaneous method. The open surgical biopsy procedure involves making an open incision to the site of the tissue of interest, cutting a sample of the tissue, and removing the tissue through the open incision. A percutaneous biopsy is performed by inserting biopsy device having a needle and a cutting device through a small incision and advancing the needle and cutting device to the site of the tissue of interest. Then, the cutting device cuts a sample of tissue, and the biopsy device captures the tissue sample and removes the sample through the small incision. Percutaneous biopsy devices have used various means to remove the tissue sample, such as simply removing the device out through the incision with the captured tissue sample, or transporting the tissue sample out through the device (e.g., using vacuum) where it can be removed or drawn through a tube to a container. One advantage of removing the tissue sample from the biopsy device is that multiple samples may be taken without having to remove the biopsy device.

The tissue sample is then examined for diagnosis by imaging the tissue sample using X-ray (while previous X-ray imaging systems recorded on film, more recent X-ray imaging system are digital and record using semiconductor receptors), MRI (magnetic resonance imaging) or other suitable imaging device. For instance, the tissue sample may be placed on an imaging substrate, such as a tissue slide or film, and then placed into the imaging device for taking an image.

Automated biopsy and imaging systems for performing a biopsy and imaging a tissue sample have also been disclosed. For example, U.S. Pat. No. 9,492,130 B2 discloses an integrated biopsy analysis system having a biopsy excision tool, a tissue sample transport mechanism for automatically transporting an excised tissue sample from the biopsy excision tool to an analysis/imaging unit, and an analysis/imaging system for automatically analyzing tissue samples such as imaging using an X-ray imaging device. U.S. Pat. No. 9,492,130 B2 is hereby incorporated by reference herein in its entirety. The disclosed system excises tissue samples, and transfers and places the excised tissue samples into a specimen holder having a plurality of tissue accepting slots for placing a plurality of different tissue samples. The imaging unit is configured to acquire images of the tissue samples in the tissue holder, such as by acquiring individual images of each tissue sample in its respective tissue accepting slot.

The biopsy excision tool of an automated biopsy system may be a motor driven biopsy device such that its operation can be automated and controlled by a controller. For example, U.S. Patent Application Publication No. US 2016/0089121 A1 discloses a motor driven biopsy device which can be controlled by a computerized, electronic controller coupled to the biopsy device. The disclosed biopsy device includes a motorized driver and a disposable biopsy needle assembly which is configured to be removably coupled to the motorized driver. This assembly provides a biopsy device in which the component coming into contact with a patient's tissue during a biopsy procedure, namely the biopsy needle assembly, can be separated from the component which does not contact the patient's tissue, namely the motorized driver. This improves and simplifies the sterilization procedure because the motorized driver does not contact biological material requiring sterilization during normal use of the biopsy device. Therefore, preparing the biopsy device for a biopsy procedure after using the biopsy device simply requires removing the used biopsy needle assembly from the driver and disposing it, and then installing a new, sterile biopsy needle assembly onto the driver. The driver may be wiped down to disinfect the surface.

The needle assembly comprises an outer cannula axially movable and rotatable relative to the needle assembly. An inner cannula is slidably received in the lumen of the outer cannula such that it is axially movable and rotatable relative to the needle assembly. The needle assembly also includes an outer cannula hub coupled to the outer cannula and an inner cannula hub coupled to the inner cannula. An inner cannula gear may also be coupled to the inner cannula for rotating the inner cannula relative to the biopsy device. Likewise, an outer cannula gear may also be coupled to the outer cannula for rotating the outer cannula relative to the biopsy device relative to the biopsy device.

The motorized driver includes a motor operatively coupled to an inner cannula drive member and an outer cannula drive member via one or more drive mechanisms. The motor and drive mechanisms are configured to move the inner cannula drive member and outer cannula drive member axially between respective proximal and distal positions relative to the biopsy device. The inner cannula drive member removably and operatively couples to the inner cannula hub such that axial movement of the inner cannula drive member effects axial movement of the inner cannula. Similarly, the outer cannula drive member removably and operatively couples to the outer cannula hub such that axial movement of the outer cannula drive member effects axial movement of the outer cannula. The motor is a reversible output motor such that activation of the motor in a first output direction drives (via the drive mechanism(s)) the inner cannula drive member and/or outer cannula drive member in a proximal axial direction. Conversely, activation of the motor in a second output direction, opposite the first output direction, drives (via the drive mechanism(s)) the inner cannula drive member and/or outer cannula drive member in a distal axial direction. The motorized driver may also include a rotatable driver gear operatively coupled to the motor via a gear drive mechanism. The driver gear operatively couples to the inner cannula gear such that activation of the motor rotates the inner cannula via the gear drive mechanism and mating driver gear and inner cannula gear. Alternatively, the motorized driver may include multiple motors, such as a first motor for driving the inner cannula drive member and a second motor for driving the outer cannula drive member.

During use of the motorized biopsy device, it is standard procedure for the biopsy needle assembly to be removed from the driver and a new biopsy needle assembly to be installed on the driver. Also, it may be necessary to remove and re-install or replace the biopsy needle assembly during operations of the automated biopsy system other than at the end of a completed biopsy procedure. When a biopsy needle assembly is being installed on the motorized driver, it is imperative that the inner cannula hub is properly aligned with the inner cannula drive member and the outer cannula hub is properly aligned with the outer cannula drive member. A misaligned needle assembly is unable to perform the intended critical biopsy procedure and may in some cases become suddenly dislodged from the driver, startling the patient and user, as well as delaying the procedure. Delaying the procedure could mean increasing the time under compression for the patient and increasing patient discomfort, and anxiety already associated with a biopsy.

Since each of the inner cannula hub and outer cannula hub are axially movable relative to the needle assembly, and each of the inner cannula drive member and outer cannula drive member are axially movable relative to the drive member, the respective hubs and drive members may not be axially aligned when removing and replacing needle assemblies on the driver. For instance, a biopsy device may be stopped during a biopsy procedure, or stopped during a setup and test procedure if the needle assembly fails during the procedure, or powered on without a needle assembly installed, with the inner cannula drive member and the outer cannula drive member in respective proximal-most axial positions, wherein a new needle assembly needs to be installed. The new needle assembly may have the inner cannula hub and the outer cannula hub at their respective distal-most positions. Upon installation of the new needle assembly, the inner cannula hub and outer cannula hub will not couple to the respective inner cannula drive member and outer cannula drive member. Accordingly, improved systems and methods are needed to ensure that the drive and needle assembly are adjusted to position the respective coupling components upon installation of a needle assembly on a motorized driver and further to minimize the instances where a needle assembly may be assembled in a misaligned state.

SUMMARY

Embodiments of the disclosed inventions are directed to systems and methods for homing an automated biopsy system having a motorized driver for installing a disposable biopsy needle assembly onto the driver such that one or more drive members on the biopsy driver properly couple with respective drive interfaces on the biopsy needle.

In one embodiment, an automated biopsy system comprises a biopsy device, which may be the same or similar to the biopsy device disclosed in U.S. patent U.S. Patent Application Publication No. US 2016/0089121, the disclosure of which is incorporated by reference in its entirety, and for all purposes. The biopsy device comprises a motorized driver having a motor and a first drive member operatively coupled to the motor for actuating the first drive member. As an example, the first drive member may be an inner cannula drive member. The first drive member is configured to operatively couple to a first needle interface of the biopsy needle assembly. For example, the first needle interface may be an inner cannula hub which is coupled to an inner cannula. The motorized driver is configured to activate the motor which in turn actuates the first drive member to thereby actuate the biopsy needle assembly via the first needle interface.

The biopsy system includes a controller operatively coupled to the motorized driver. For instance, the controller may be a computerized, electronic controller having a microprocessor, and input/output ports for controlling the operation of the driver. The controller is configured to perform a homing process to activate the driver to position the first drive member in a first drive member home position to properly couple to a first needle interface of a new biopsy needle assembly to be installed on the driver.

The homing process comprises first determining a system test failure, or a needle removal condition in which a biopsy needle assembly currently installed on the motorized driver has been or should be removed from the motorized driver. For instance, the biopsy system may fail a test during setup and/or test procedure, or the currently installed biopsy needle may have completed a biopsy procedure and needs to be changed for a subsequent procedure or has already been uninstalled for being replaced for a subsequent procedure, or it has a fault and needs to be replaced.

The homing process then includes performing a driver homing to position the first drive member in the first drive member home position for receiving a second biopsy needle assembly to be installed on the motorized driver. The driver homing step includes operating the motorized driver to position the first drive member in the first drive member home position.

In another aspect, the new biopsy needle assembly includes a pre-set first needle interface pre-positioned in a first needle home position for operatively coupling with the first drive member in the first drive member home position. For instance, the biopsy needle assembly may include a transport lock which maintains the first needle interface in the first needle home position while the biopsy needle assembly is packaged in a sterile packaging and during handling for installing the biopsy needle assembly on the motorized driver.

In another aspect, the biopsy system may be configured to perform the driving homing prior to the biopsy needle assembly being removed from the motorized driver, or after removing the biopsy needle assembly. In a related feature, the biopsy system includes a needle installed sensor for detecting whether a biopsy needle assembly is installed or not. The needle sensor is operatively coupled to the controller. The controller receives a signal from the needle sensor and can determine if a biopsy needle assembly has been removed from the driver, and/or installed on the driver based on the signal. The homing process further includes determining that the biopsy needle assembly has been removed from the driver. The controller is configured to perform the driver homing after determining that the biopsy needle assembly has been removed from the driver.

In other aspect, the biopsy system may be configured to display a message on a user interface display with instructions to remove the biopsy needle assembly from the motorized driver, and/or to prompt a user to select whether to replace a first biopsy needle installed on the driver with a second biopsy needle assembly.

In yet another aspect, the biopsy system may be configured to provide an audio signal prior to performing the homing process that warns the user that the biopsy system is about to perform the homing process. The audio signal warns the user that the biopsy device is going to operate the motorized driver, which may include the movement of gears, drive members and/or other components, so the user can keep clear to avoid being injured or damaging the biopsy system or its components. The audio signal may be one or more chimes or beeps (e.g., three chimes or beeps), or other suitable audio signal.

In still another aspect of the disclosed biopsy system, the controller may be configured to perform the homing process for each of a plurality of homing modes. For instance, the controller may be configured to perform the homing process in any one or more of the following homing modes, including a first homing mode, a second homing mode, a third homing mode, and/or a fourth homing mode.

In the first homing mode, the homing process comprises: detecting that the system was powered ON from a powered OFF state with the biopsy needle installed on the motorized driver; displaying a message on a user interface display of the biopsy system to remove the biopsy needle assembly from the motorized driver, detecting that the biopsy needle assembly has been removed from the motorized driver, and after determining that the biopsy needle assembly has been removed, performing the driver homing.

In the second homing mode, the homing process comprises: verifying that the biopsy system has entered a standby mode after a biopsy procedure has been performed using the first biopsy needle assembly installed on the motorized driver, detecting that the first biopsy needle assembly has been removed from the motorized driver, and after detecting that the first biopsy needle assembly has been removed, performing the driver homing.

In the third homing mode, the homing process comprises: detecting, during one of a biopsy, lavage, or aspirate mode, that the first biopsy needle assembly has been removed from the motorized driver, after detecting that the first biopsy needle assembly has been removed, prompting a user to select, through the user interface, whether to install a second biopsy needle assembly, upon receiving a user selection to install the second biopsy needle assembly, performing the driver homing, and when not receiving a user selection to install the second biopsy needle assembly, leaving the first drive member in a same position as when the first biopsy needle was removed.

In the fourth homing mode, the homing process comprises: determining, during a setup and test procedure of the biopsy system, that a test fail condition has been met, and after determining that the test fail condition has been met, performing the driver homing while the first biopsy needle assembly remains installed on the motorized driver.

In another feature of the disclosed biopsy system, the motorized driver may include a second drive member configured to operatively couple to a second needle interface of the biopsy needle assembly. The second drive member is operatively coupled to the motor for actuating the second drive member. The second drive member is configured to operatively couple to a second needle interface of the biopsy needle assembly. For instance, the second needle interface may be an outer cannula hub which is coupled to an outer cannula of the biopsy needle assembly. The motorized driver is further configured to activate the motor to actuate the second driver member to thereby actuate the biopsy needle assembly via the second needle interface.

The homing process includes homing the second drive member to properly couple to the second needle interface when a biopsy needle assembly is installed onto the driver.

The homing process further comprises activating the motorized driver to position the second drive member in a second driver member home position for receiving a biopsy needle assembly. The biopsy needle assembly may include a pre-set second needle interface in a second needle home position for operatively coupling to the second drive member in the second drive member home position.

Further embodiments of the disclosed inventions are directed to methods for homing an automated biopsy driver in order to install a disposable biopsy needle assembly onto the driver such that one or more drive members on the driver are positioned to properly couple with respective drive interfaces on the biopsy needle. In one embodiment, the method comprises determining a system test failure, or needle removal condition in which a biopsy needle assembly installed on a motorized driver of the automated biopsy system has been or should be removed from the motorized driver. The motorized driver has a first drive member coupled to a first needle interface of the biopsy needle assembly. After determining the needle removal condition, a driver homing is performed. The driver homing comprises operating the motorized driver to position the first drive member in a first drive member home position for receiving a new biopsy needle assembly to be installed on the motorized driver.

In another aspect of the method embodiment, the new biopsy needle assembly includes a pre-set first needle interface in a first needle home position for operatively coupling with the first drive member in the first drive member home position.

In additional aspects of the method embodiment, the method may include any one or more of the additional aspects and features described herein for the automated biopsy system having a motorized driver for installing a disposable biopsy needle assembly onto the driver such that one or more drive members on the biopsy drive properly couple with respective drive interfaces on the biopsy needle assembly.

BRIEF DESCRIPTION OF THE DRAWINGS

The foregoing and other aspects of embodiments of the disclosed inventions are described in further detail with reference to the accompanying drawings, wherein like reference numerals refer to like elements and the description for like elements shall be applicable for all described embodiments wherever relevant:

FIG. 4 is a top, side, perspective view of a needle assembly of the automated biopsy system of FIG. 1, according to one embodiment;

FIG. 5 is a bottom, side, perspective view of the needle assembly of the automated biopsy system of FIG. 1, according to one embodiment;

FIG. 8 illustrates a flow chart of a method for using the automated biopsy system of FIG. 1, according to another embodiment;

FIG. 9 illustrates a flow chart of a method for using the automated biopsy system of FIG. 1, according to another embodiment;

DETAILED DESCRIPTION

Figure 1:
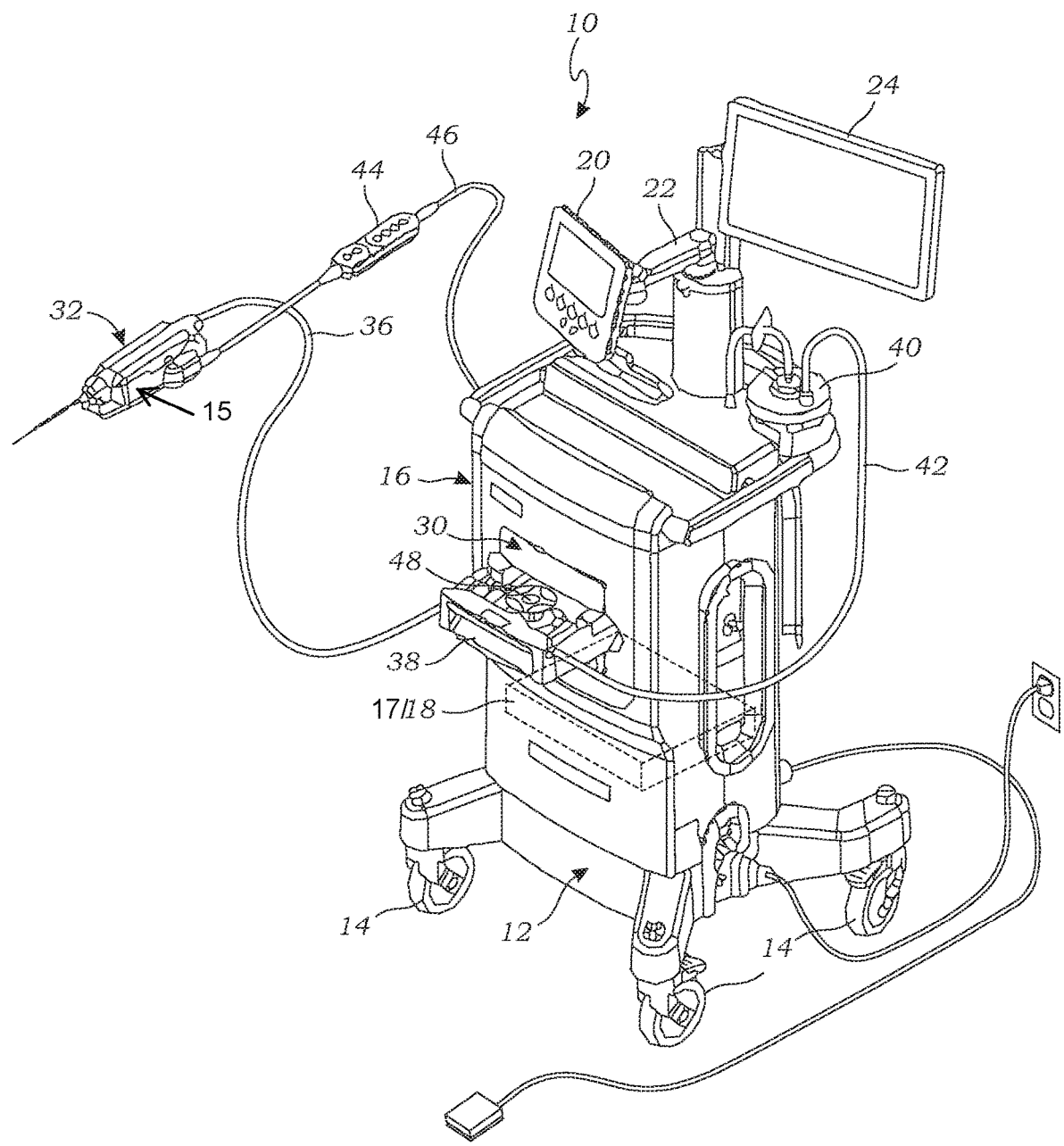
FIG. 1 is a front, right, perspective view of an automated biopsy system, according to one embodiment.
Figure 2:
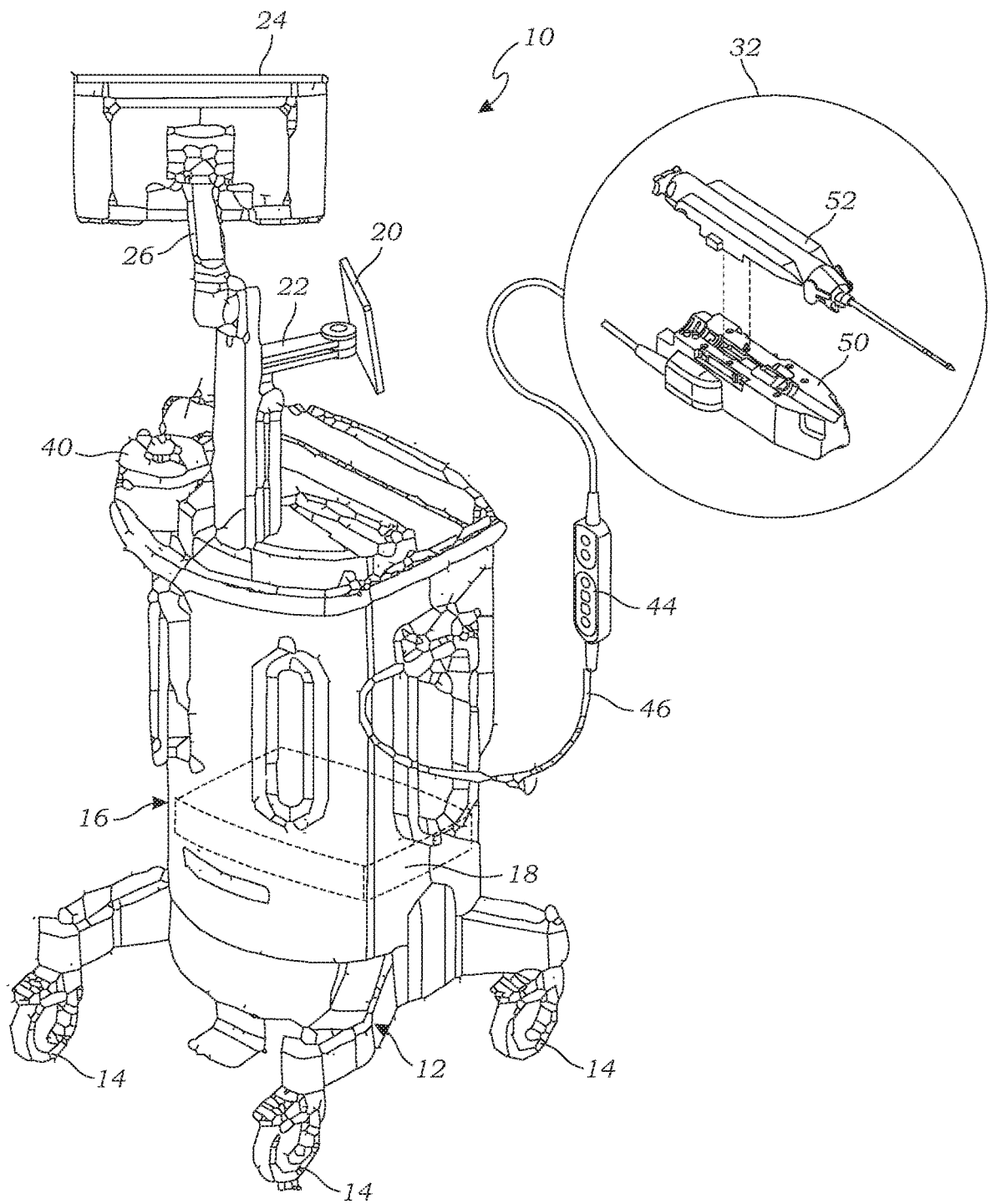
FIG. 2 is a back, left, perspective view of the automated biopsy system of FIG. 1, according to one embodiment.

FIGS. 1 and 2 illustrate an automated biopsy system 10 for automatically performing a biopsy to excise a tissue sample, and imaging the tissue sample. The biopsy system 10 is a first of its kind integrated biopsy system that can both perform a biopsy and an image verification of the excised tissue sample, as part of a single system in an automated fashion. The biopsy system 10 is a cart mounted, portable system which can easily be moved around a clinic or hospital. The biopsy system 10 includes a cart 12 having four casters 14 with locking brakes to hold the system 10 in place. A system cabinet 16 is mounted on the cart 12. The system cabinet 16 supports and/or houses the various components of the biopsy system 10. A computer system 17, 18 is mounted inside the system cabinet 16. The computer system 17, 18 includes a microprocessor, and a plurality of input and output ports for operatively coupling the components of the biopsy system to the computer system 18. The computer system 17,18 may include one or more computer systems. For example, an imaging display computer 18 and a biopsy console computer 17. The biopsy console computer activates motion and can provide audio signal, while the imaging display computer can interface with external systems for transmission of captures images.

The biopsy system 10 further includes a biopsy control panel 20 mounted to the system cabinet 16 using an adjustable display mount 22. The biopsy control panel 20 is operatively coupled to the computer system 18 in order to communicate graphics and commands between the biopsy control panel 20 and the computer system 18. The biopsy control panel 20 is configured to control, and display the status of, a biopsy procedure being performed by the biopsy system 10. The biopsy control panel 20 includes a video display, such as an LED monitor, LCD monitor or other suitable monitor, and multiple input buttons for entering commands to the computer system 18 for controlling the operation of a biopsy procedure.

The biopsy system 10 also has an imaging display screen 24 mounted to the system cabinet 16 via an adjustable display screen mount 26 which provides a user interface for viewing, annotating, saving, and exporting radiographic images of tissue samples obtained by the biopsy system 10. The imaging display screen 24 is a touchscreen display, such as an LCD touchscreen, LED touchscreen, or other suitable touchscreen display. The imaging display screen 24 is operatively coupled to the computer system 17,18 in order to communicate graphics (including radiographic images of tissue samples) and commands between the imaging display screen 24 and the computer system 17,18.

As will be further described with reference to FIGS. 6-12, the computer system 18, in various embodiments, determines a needle removal condition, or a system failure, in which a biopsy needle assembly, which is further described below, has been or should be removed, for various reasons, such as due to misalignment. This may occur under several different conditions. The computer system 18 detects the condition, may stop the operation, and may prompt the user, via the biopsy control panel 20, to perform various steps to correct for misalignment, such as performing homing procedures, removing and re-installing or replacing the biopsy needle assembly. The steps for performing the homing procedures, and the steps for correcting misalignment may be displayed via the biopsy control panel 20.

The biopsy system 10 also has a biopsy subsystem for excising a tissue sample, and transporting the tissue sample to an imaging/analysis unit 30 of the biopsy system 10. The biopsy subsystem includes a biopsy device 32, and a tissue sample processing system for transporting tissue samples to the imaging/analysis unit 30 from the biopsy device 32 and handling tissue samples during imaging by the imaging/analysis unit 30. The tissue sample processing system includes a tissue handling assembly 38 connected to the biopsy device 32 by flexible suction tubing 36, and a suction canister 40 connected to the tissue handling assembly 38 by flexible vacuum tubing 42. The suction canister 40 provides a vacuum source for transporting tissue sample excised by the biopsy device 32 to the tissue handling assembly 38.

The tissue handling assembly 38 includes a tissue filter assembly 48 for receiving a plurality of tissue samples excised by the biopsy device 32 and transported to the tissue filter assembly 48 via the suction tubing 36. The tissue filter assembly 48 includes a housing in which a tissue holder is rotatably mounted. The tissue holder may be rotated using any suitable actuator, such as a magnetic drive system which rotates the tissue holder 48 using a magnetic field which exerts magnetic force on a magnet or magnetizable element disposed on the tissue holder 48. The tissue holder has a plurality of tissue storage compartments, such as 10-30 tissue storage compartments or other suitable number, arranged angularly around the tissue holder. In this exemplary embodiment, the tissue holder has a circular shape such that the tissue storage compartments are wedge-shaped (i.e., pie-shaped, sector of a circle), or a sector of an annulus shape in the case that the central part of each tissue storage compartment does not extend all the way to the axis. The bottom of the tissue holder has a tissue filter comprising a porous filter material. The tissue filter may be a single filter, such as a filter sheet, which covers the entire bottom of the tissue holder, or alternatively, the tissue filter may be individual filters disposed on the bottom of each tissue storage compartment.

The tissue filter assembly 48 has an inlet port which is in fluid communication with the biopsy device 32 via the suction tubing 36. The tissue filter assembly 48 has an outlet port which is in fluid communication with the suction canister 40 via the vacuum tubing 42.

The tissue handling assembly 38 is operatively coupled to the computer system 18 such that the computer system 18 can control the operation of the tissue handling assembly 38, including the tissue filter assembly 48. As the biopsy device 32 excises tissue samples, the computer system 18 rotates the tissue filter assembly 48 to deposit individual tissue samples into respective tissue storage compartments of the tissue filter assembly 48.

The biopsy system 10 also includes an integrated imaging/analysis system 30 configured to capture images of tissue samples contained in each of the tissue storage compartments of the tissue filter assembly. The imaging/analysis system 30 is also operatively coupled to the computer system 18 in order to control the operation of the imaging/analysis system 30 and to communicate digital images captured by the imaging/analysis system to the computer system 30. The imaging/analysis system 30 includes an imaging device, such as an X-ray imaging device, or other suitable imaging device for capturing images of the excised tissue samples contained in the storage containers of the tissue filter assembly. The imaging device may be configured to capture an image of a tissue sample in a single storage compartment positioned in the imaging field of the imaging device, and then the tissue filter assembly may be rotated to position the next tissue storage compartment in the imaging field of the imaging device. The process is repeated until images have been acquired for all of the respective tissue samples in each of the tissue storage compartments. Alternatively, the imaging device may be configured to image all of the tissue samples in all of the storage containers at once by taking a single image of all of the storage containers. The single image may then be processed by the computer system 18 to identify the individual containers and separating each image from each container.

One embodiment of a suitable tissue handling assembly 38 having a tissue filter assembly 48 and an integrated 30 imaging/analysis system which may be used in the biopsy system 10 of the disclosed inventions are described in more detail in U.S. Pat. No. 9,492,130, the disclosure of which is incorporated by reference in its entirety.

The biopsy device 32 is operatively coupled to the computer system 18 by a biopsy device cable 46 and remote control 44. The biopsy device 32 may include a device driver computer 15 which receives activation commands from the computer system 18 and drives the biopsy device 32. The device driver computer 15 can continue to operate even if the communication is interrupted with the computer system 18. The remote control 44 is configured to transmit control commands to the computer system 18 to control the operation of the biopsy device 32. Alternatively, or additionally, the remote control 44 may be configured to transmit control commands to the device driver computer 15 to operate the biopsy device 32.

Figure 3:
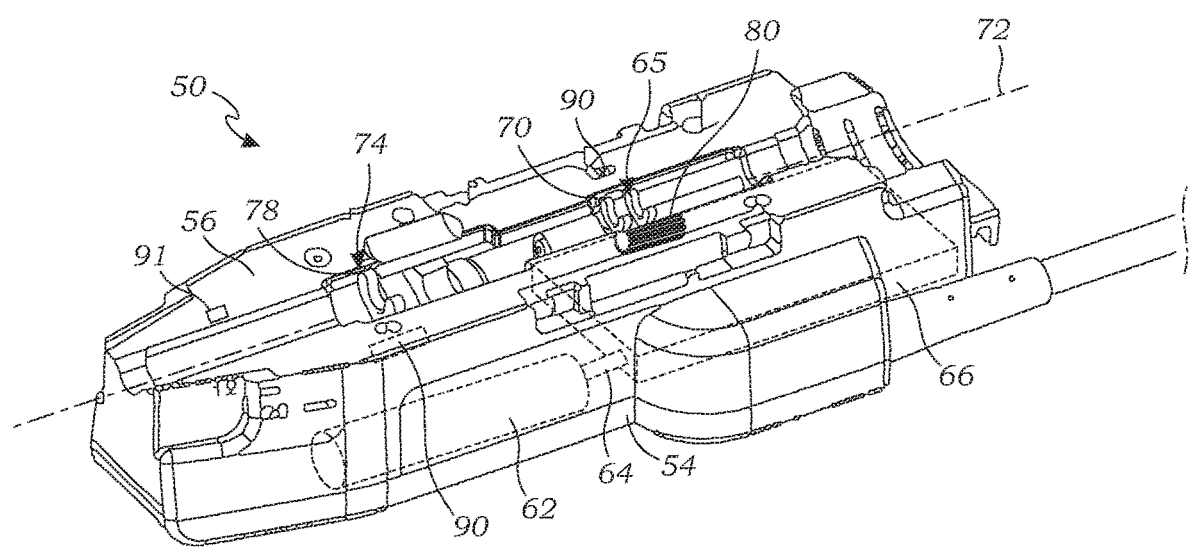
FIG. 3 is a top, side, perspective view of a motorized driver of the automated biopsy system of FIG. 1, according to one embodiment.

As depicted in FIG. 2, the biopsy device 32 comprises two main components, a motorized driver 50 and a biopsy needle assembly 52, which are removably attachable to each other to form the biopsy device 32. Turning now to FIGS. 3-5, the biopsy device 32 will now be described in more detail. The biopsy device 32 may the same as, or similar to, the motor driven biopsy device shown and described in U.S. Patent Application Publication No. US 2016/0089121 A1, the disclosure of which is incorporated by reference herein in its entirety.

As shown in FIG. 3, the motorized driver 50 comprises a driver housing 54 having a top surface 56 configured to mate with a bottom surface 58 of a needle assembly housing 60 of the needle assembly 52. The motorized driver 50 has a motor 62 mounted to the driver housing 54. The motor 62 is a reversible motor having a reversible output shaft 64. The motorized driver has a first drive member 65 configured to removably and operatively couple to a first needle interface 68 of the needle assembly 52. The first drive member 65 comprises a pair of forks 70 which are slidably mounted to the driver housing 54 such that the first drive member 65 is movable axially along a longitudinal axis 72 between a proximal position and a distal position. As used herein, the term "proximal" and its other forms, and "distal" and its other forms, are referenced such that a first position to the left of a second position is "proximal" to the second position, and a first position to the right of a second position is "distal" to the second position, based on the orientation of the device as shown in FIGS. 3-5. The first drive member 65 is operatively coupled to a drive mechanism 66. The drive mechanism 66 is operatively coupled to the motor 62 via the output shaft 64. The drive mechanism 66 is configured to convert the rotational motion of the output shaft 64 to move the first drive member 65 axially between the proximal position and distal position.

The motorized driver 50 also has a second drive member 74 configured to removably and operatively couple to a second needle interface 76 of the needle assembly 52. The second drive member 74 comprises a fork 78 which is slidably mounted to the driver housing 54 such that the second drive member 74 is movable axially along a longitudinal axis 72 between a proximal position and a distal position. The second drive member 74 is also operatively coupled to the drive mechanism 66. The drive mechanism 66 is configured to transform the rotational motion of the output shaft 64 to move the second drive member 74 axially between its proximal position and distal position. The drive mechanism 66 is configured to move the second drive member 74 both independently of moving the first drive member 65 and/or jointly with moving the first drive member 65. For example, the drive mechanism 66 may comprise an adjustable selector, such as an adjustable cam, to lock and unlock the motion of the first drive member 65 to the second drive member 74.

The driver 50 is configured to load the second drive member 74 in a firing position by compressing a firing spring coupled to the second drive member 74, and to fire the second drive member by releasing the second drive member 74 thereby allowing the expansive force of the spring to fire the second drive member 74. The motor 62 is coupled to the second drive member 74 by an adjustable cam which is adjustable between a locked position which couples the second drive member 74 to the motor 62 and a release position which releases the second drive member 74 from being coupled to the motor 62. With the cam in the locked position, the motor 62 moves the second drive member 74 proximally to the firing position. As the driver 50 moves the second drive member 74 proximally along the longitudinal axis 72, the movement of the second drive member 74 compresses the firing spring. The second drive member 74 is fired by adjusting the cam to the release position thereby allowing the expansive force of the spring to quickly move the second drive member 74 distally to a fired position.

The drive mechanism 66 may also include a rotatable driver gear 80, such as a pinion gear, operatively coupled to the motor 62 via the drive mechanism 66. The driver gear 80 operatively couples to the first needle interface 68 (as described below, the first needle interface 68 comprises an inner cannula gear 82 which couples to the driver gear 80) such that activation of the motor 62 rotates the first needle interface 68 via the drive mechanism 66 and the mating driver gear 80 and first needle interface 68.

The motorized driver 50 has one or more encoders 90 for detecting the axial position of each of the first drive member 65 and the second drive member 74. The motorized driver 50 also has a needle sensor 91 for detecting whether a biopsy needle assembly 52 is installed or not installed on the driver 50. The needle sensor 91 is operatively coupled to the computer system 18. The needle sensor 91 transmits a signal to the computer system 18 from which the computer system 18 can determine if a biopsy needle assembly 52 has been removed from the driver 50, and/or installed on the driver 50.

As shown in FIGS. 4 and 5, the biopsy needle assembly 52 comprises a needle assembly housing 60 having a bottom surface 58 configured to mate with the top surface 56 of the motorized driver 50. The biopsy needle assembly 52 includes an outer cannula 84 slidably and rotatably coupled to the needle assembly housing 60. The outer cannula 84 is slidable axially relative to the needle assembly housing along the longitudinal axis 72. The outer cannula 84 has an outer cannula aperture 85 disposed near a distal end of the outer cannula 84 and a trocar tip 87 on the distal end of the outer cannula 84. The outer cannula aperture 85 is configured to cut tissue specimens from adjacent tissues during a biopsy procedure, and to receive the excised tissue specimens into the lumen of the outer cannula 85. The biopsy needle assembly 52 includes the second needle interface 76 which is coupled to the outer cannula 84 such that axial movement of the second needle interface 76 causes like axial movement of the outer cannula 84. The second needle interface 76 comprises an outer cannula hub 76 having an outer cannula gear 77. The outer cannula hub 76 is configured to couple to the fork 78 of the second drive member 74.

The biopsy needle assembly 52 may include a separate introducer portion 89 of the outer cannula 84, which assembles to the needle assembly 52 with the introducer portion 89 coupling to the outer cannula 84.

The biopsy needle assembly 52 also has an inner cannula 86 slidably and rotatably received in the outer cannula 84. The inner cannula 86 is slidable axially along the longitudinal axis 72 relative to the outer cannula 84 and the needle assembly housing 60. The first needle interface 68 is coupled to the inner cannula 86 such that axial movement of the first needle interface 68 causes like axial movement of the inner cannula 86. The first needle interface 68 comprises an inner cannula hub 68 having an inner cannula gear 82.

The biopsy needle assembly 52 may also have a thumbwheel 88 coupled to the distal end of the outer cannula 84 in order to allow manual rotation of the outer cannula 84.

The inner cannula 86 is axially slidable relative to the outer cannula 84 such that the inner cannula 86 can close the outer cannula aperture 85.

The biopsy needle assembly 52 may include pre-set positions for the first needle interface 68 and second needle interface 76 such that they are pre-positioned in a respective first needle home position and second needle home position for operatively coupling with the respective first drive member 65 and second drive member 74 in their respective first drive member home position and second drive member home position. The biopsy needle assembly 52 may include a transport lock which maintains the first needle interface 68 in the first needle home position and the second needle interface 76 in the second needle home position when the biopsy needle assembly 52 is a sterile packaging and during handling while installing the biopsy needle assembly 52 on the motorized driver 50.

As described herein, the biopsy needle assembly 52 is designed to be disposable between each biopsy procedure using the biopsy system 10 in order to provide a sterile biopsy needle assembly 52. Accordingly, a used biopsy needle assembly 52 is removed and a new biopsy needle assembly 52 is installed on the motorized driver 50 between each biopsy procedure. In addition, there may be other conditions, as described in more detail below, when a biopsy needle assembly 52 is replaced and/or removed and reinstalled during the use of the biopsy system 10. As can be seen by viewing FIGS. 3 and 5, when assembling the biopsy needle assembly 52 onto the motorized driver 50, the first drive member 65 and second drive member 74 must be properly aligned with the respective first needle interface 68 and second needle interface 76.

A biopsy procedure including the different modes of operation will now be described for reference. Before a procedure is started, a user (typically a biopsy technician), will power on the biopsy system, the driver will perform a homing process as further described below. The user will then assembly the needle to the driver. The display screen shows that the needle and the device driver are properly installed. The vacuum lines and the tissue holder are then connected and installed.

As part of the biopsy procedure, the biopsy system 10 can enter or be placed into any of the following modes. First, Standby mode, where the vacuum is off, the needle aperture is closed and the device cannot be fired and images cannot be taken. Standby mode can be used so that the biopsy system 10 can be safely assembled/dissembled and prepared for the biopsy procedure without the biopsy device 32 accidently being fired. Second, the Setup and Test mode, in which the vacuum is tested, the user can be asked to confirm the saline flow, and a test cutting cycle can also performed. Test mode is used before a biopsy procedure to verify proper operation of the biopsy system 10 before a biopsy is completed. This prevents any delays and any unnecessary or erroneous steps during the procedure. Once a proper test is completed, the biopsy system can enter into the third mode, Biopsy mode. In Biopsy mode, the biopsy device 32 is used for tissue acquisition. After the tissue has been acquired, the biopsy system 10 enters into Lavage mode, the fourth mode. Lavage mode is used to irrigate the cavity and to clear the biopsy device of tissue. The biopsy system 10 can turn the vacuum on, open the aperture, open the saline pinch valve, and close the aspiration valve in order to push saline through the aperture. If there is a need for additional aspiration, Aspirate mode, the fifth mode, can be selected to vacuum the cavity. The biopsy system 10 can turn the vacuum on, open the aperture, close the saline pinch valve, and open the aspiration valve in order to push air through the aperture. Aspirate mode can also be used, or be entered into, after removing needle from the breast, to clear the aperture of the biopsy device 32. After completion of Biopsy, Lavage and Aspirate modes, the biopsy system 10 may then enter Standby mode in preparation for the next procedure.

Accordingly, the computer system 18 is configured to perform a homing process to activate the motorized driver 50, and/or to "fire" the driver 50, to position the first drive member 65 and the second drive member 74 in a first drive member home position and second driver member home position, respectively, such that the first drive member 65 and second driver member 74 properly couple to the respective first needle interface 68 and second needle interface 76 of a biopsy needle assembly 52 being installed on the driver 50. In one embodiment, the first drive member 65 is homed by activating the motorized driver 50 to move the first drive member 65 to the first drive member home position, and the second drive is homed by "firing" the second drive member 74 to move the second drive member home position. As described herein, the homing process may be performed automatically by the biopsy system 10, or it may perform in the homing process in response to an instruction from the user.

The first drive member home position and second drive member home position may be their respective distal-most positions, or proximate their distal-most positions, which may be set one or more stops provided on the drive 50. For instance, the first drive member home position may be a position obtained by the driver 50 moving the first drive member to a calibration position, such as a "zeroed" position using the encoders 90, and then the driver moving the first drive member 65 to the drive member home position. The second drive member 74 may be positioned in the second drive member home position similarly.

Alternatively, the driver 50 may position the second drive member 74 in the second drive member home position by "firing" the second drive member, as described above. Regardless of the specific position, the first drive member home position and second drive member home position are set to align with the respective pre-set first needle interface home position and second needle interface home position. For example, the pre-set first needle interface home position and pre-set second needle interface home position may be their respective distal-most positions relative to the needle assembly housing 60. Alternatively, the first needle interface home position and/or second needle interface home position may be a position proximate their respective distal-most positions. The computer system 18 may utilize the encoders 90 to determine the positions of the first drive member 65 and second drive member 74, and to operate the drive 50 to position the first drive member 65 and second drive member 74 in their respective home positions. The homing process allows for proper alignment and if the homing process is not completed properly, the biopsy system 10 alerts the user and the biopsy procedure does not commence. This is a safety feature to make sure that the biopsy device 32 will operate properly.

Figure 6:
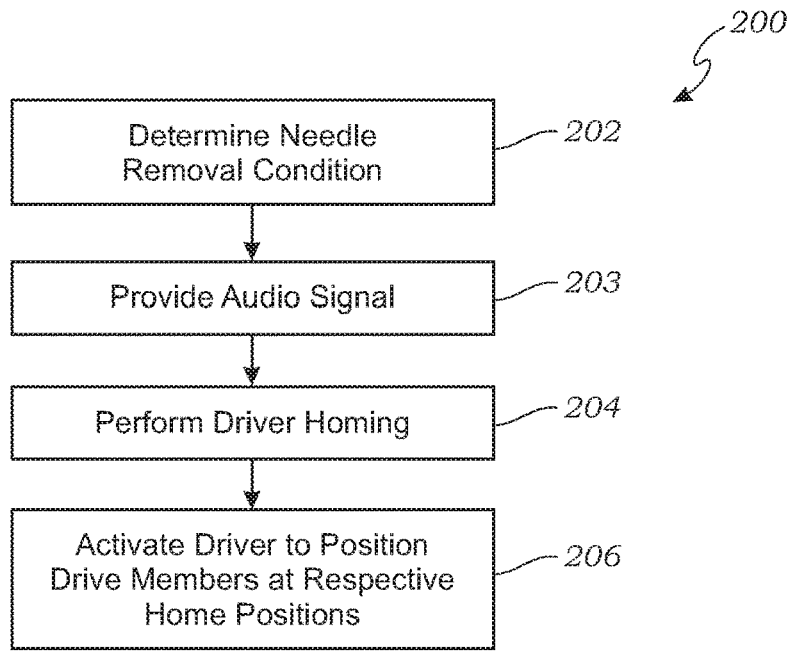
FIG. 6 illustrates a flow chart of a method for using the automated biopsy system of FIG. 1, according to one embodiment.

Turning to the flow diagram of FIG. 6, in one embodiment, a general homing process 200 is shown. The homing process 200 comprises a step 202 in which the computer system 18 determines a needle removal condition in which a biopsy needle assembly 52 currently installed on the motorized driver 50 has been or should be removed from the motorized driver 50. This may occur under several different conditions. For one, the biopsy system 10 has successfully completed a biopsy procedure and obtained the desired tissue samples and the currently installed biopsy needle assembly 52 needs to be changed for a subsequent procedure. Other such conditions may include that the biopsy needle assembly 52 has been removed as detected by the computer system 18 via the needle sensor 91, or a fault in a biopsy procedure and/or the installed biopsy needle assembly 52 has been detected.

Optionally, at step 203, the computer system 18 may provide an audio signal that warns the user that the biopsy system 10 is about to operate the biopsy device 32, including operating the motorized driver 50. The audio signal warns the user that the biopsy device 32 is going to operate, which may include the movement of gears, drive members and/or other components, so the user can keep clear to avoid being injured or damaging the biopsy system 10 or its components. The audio signal may be one or more chimes or beeps (e.g., three chimes or beeps), or other suitable audio signal.

At step 204, the homing process 200 includes performing a driver homing to position the first drive member 65 in the first drive member home position and to position the second drive member 74 in the second drive member home position. At step 206, the driver homing includes operating the motorized driver 52 to position the first drive member 65 in the first drive member home position, and operating the motorized driver 52 to position the second drive member 74 in the second drive member home position. Depending on the configuration of the motorized driver 50, the homing of the first drive member 65 and second drive member 74 may be accomplished by a single operation of the motorized driver 50, or multiple operations of the motorized driver 50. Alternatively, the second drive member 74 may be positioned in the second drive member home position by the driver 50 firing the second drive member 74, as described above.

The biopsy system 10 may be configured to perform the driving homing prior to the biopsy needle assembly 52 being removed from the motorized driver 50, or after removing the biopsy needle assembly 52. In the case that the homing process 200 is configured to perform the homing process after removing the biopsy needle assembly 52, the homing process 200 includes a step of determining that the biopsy needle assembly 52 has been removed from the driver 50 prior to performing the driver homing at step 206.

The computer system 18 is also configured to perform the homing process for each of a plurality of homing modes which may occur under various operating conditions of the biopsy system 10. In one embodiment, the computer system 18 is configured to perform the homing process in any one or more of four different homing modes. A first homing mode is performed when the biopsy system 10 detects that the biopsy system 10 was powered on with a biopsy needle assembly installed on the motorized driver. A second homing mode is typically performed when the user removes the biopsy needle assembly 52 at the end of a biopsy procedure while the biopsy system 10 is the Standby mode. A third homing mode is performed when the biopsy system 10 detects that the biopsy needle assembly 52 has been removed during one of the Biopsy, Lavage or Aspirate modes of the biopsy system 10. Removal of the needle assembly 52 in Biopsy, Lavage or Aspirate modes is typically an abnormal and non-recommended procedure because the aperture of the needle assembly 52 may be open. Nonetheless, a user may remove the needle assembly during these modes due to an abnormal event or condition. A fourth homing mode is performed is performed when the biopsy system 10 determines that that the biopsy needle assembly 52 needs to be removed, or has been removed, while the biopsy system 10 is in the Setup and Test mode.

Figure 7:
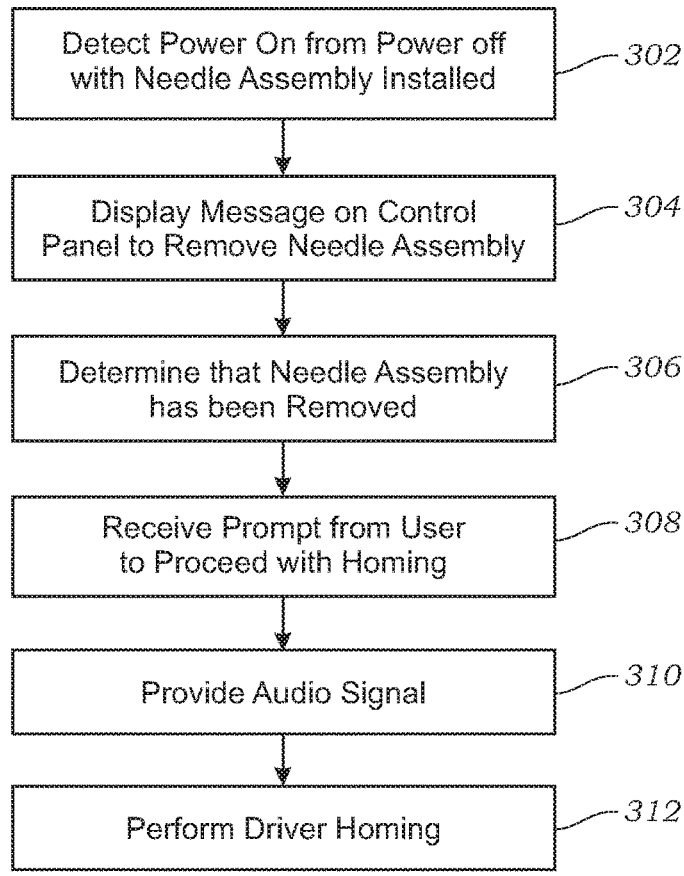
FIG. 7 illustrates a flow chart of a method for using the automated biopsy system of FIG. 1, according to another embodiment.
Figure 11:
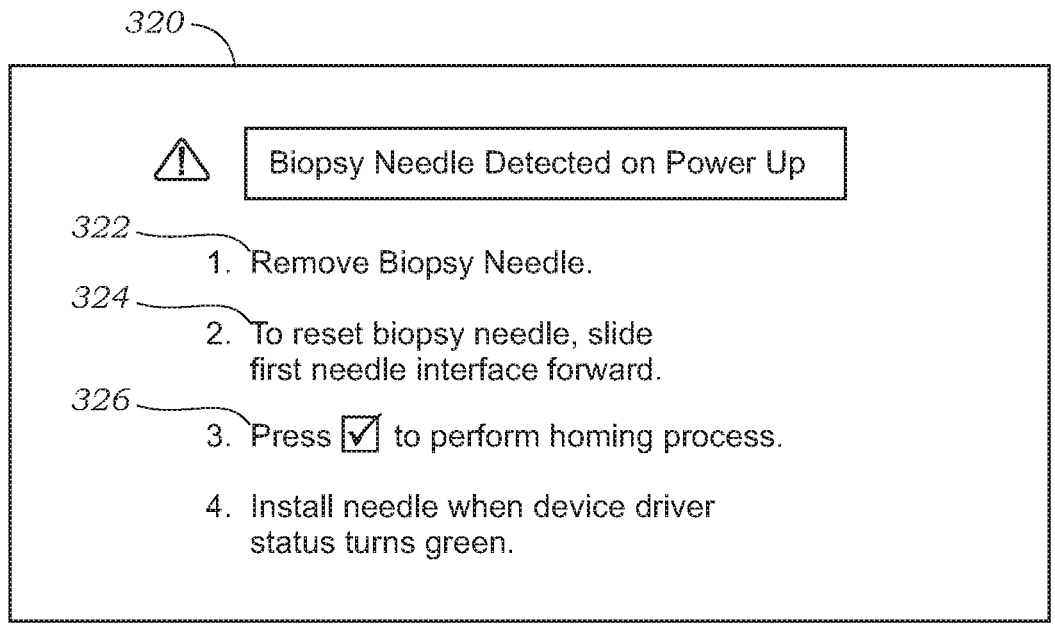
FIG. 11 illustrates a message screen which is displayed during the method illustrated in FIG. 7, according to another embodiment.
Figure 12:
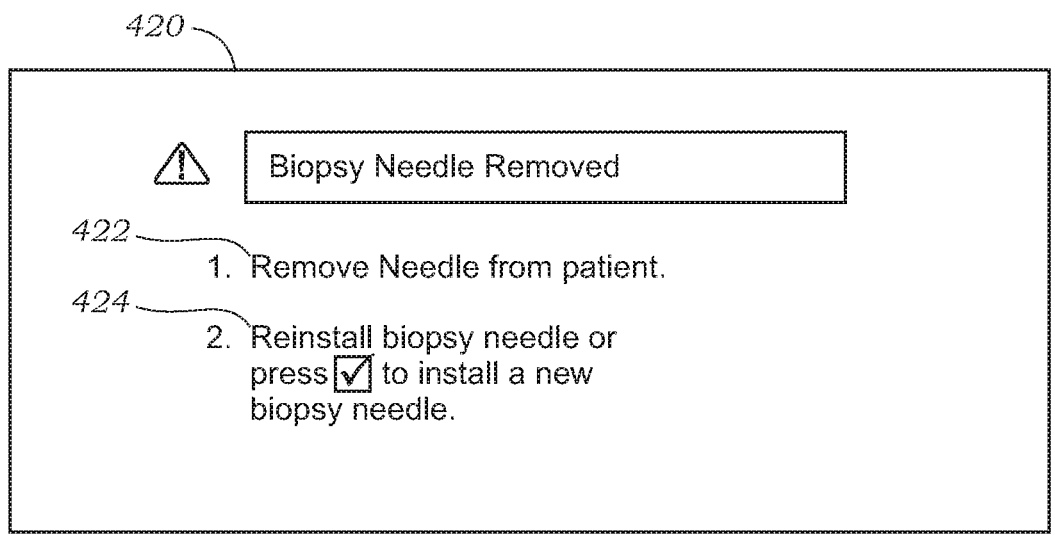
FIG. 12 illustrates a message screen which is displayed during the method illustrated in FIG. 9, according to another embodiment.

Turning to FIG. 7, in the first homing mode, the homing process 300 comprises step 302 in which the computer system 18 detects that the biopsy system 10 was powered on from a powered off state with a biopsy needle assembly 52 installed on the motorized driver 50. Upon powering on the biopsy system 10, the computer system 18 detects whether a biopsy needle assembly 52 is installed on the driver 50 using the needle sensor 91. At step 304, the computer system 18 displays a message screen 320 on the biopsy control panel 20, as depicted in FIG. 11. The message screen 320 includes an instruction 322 instructing the user to remove the biopsy needle assembly 52 from the motorized driver 50. The message screen 320 includes a message 324 advising the user that the biopsy needle assembly 52 can be reset to position the first and second needle interfaces 68, 76 in their respective home positions.

At step 306, the computer system 18 determines that the biopsy needle assembly 52 has been removed from the motorized driver 50 using the needle sensor 91. Optionally, at step 308, the computer system 18 may require the user to prompt the biopsy system 10 to proceed to the homing process. For example, the message screen 320 may display a prompt 326 which the user selects to instruct the system to proceed to the homing process. After the user selects the prompt to proceed with the homing process, at step 310, the computer system 18 may provide an audio signal that warns the user that the biopsy system 10 is about to operate the biopsy device 32, same or similar to the audio signal at step 203, described above.

At step 312, after determining that the biopsy needle assembly 52 has been removed and optionally receiving the prompt to proceed to the homing process, the computer system 18 performs the driver homing as described in steps 204 and 206 above. This homing mode is performed to insure proper alignment before the start of a biopsy procedure using the biopsy device 10. The workflow allows for homing the driver 50 first, then installing the needle assembly 52. If the proper procedure is followed, this detection step prevents misalignment from occurring.

Turning to FIG. 8, in a second homing mode, the homing process 400 is performed. Typically, the user removes the biopsy needle assembly 52 at the end of a biopsy procedure while the biopsy system 10 is in the Standby mode. In order to avoid misalignment for the next procedure, the biopsy system 10 automatically homes the motorized driver 50 upon removal of the needle assembly 32 while in the Standby mode. This ensures that the first and second drive members 65, 74 are in a ready-position for a new needle assembly 52 to be installed on the driver 50.

The homing process 400 comprises step 402 in which a biopsy procedure is performed using the biopsy system 10. At step 404, after performing the biopsy procedure, using the biopsy needle assembly 52 installed on the motorized driver 50, the computer system 18 verifies that the biopsy system 10 has entered the Standby mode. As explained above, the Standby mode is a mode in which the system 10 has completed a biopsy procedure and is powered on, and is awaiting preparation for a new or the next biopsy procedure. After the user selects the prompt to proceed with the homing process, at step 310, the computer system 18 may provide an audio signal that warns the user that the biopsy system 10 is about to operate the biopsy device 32, same or similar to the audio signal at step 203, described above. At step 406, the computer system 18 determines that the biopsy needle assembly 52 has been removed from the motorized driver 50 using the needle sensor 91. After determining that the needle assembly 52 has been removed, at step 407, the computer system 18 may provide an audio signal that warns the user that the biopsy system 10 is about to operate the biopsy device 32, same or similar to the audio signal at step 203, described above. At step 408, the computer system 18 performs the driver homing as described in steps 204 and 206 above.

Referring now to FIG. 9, in a third homing mode, the homing process 500 comprises a step 502 in which the computer system determines, during one of the Biopsy, Lavage or Aspirate modes of the biopsy system 10, that the biopsy needle assembly 52 has been removed from the motorized driver 50 by the user, same or similar to step 306 described above. Removal of the biopsy needle assembly 52 in these modes is not recommended because the aperture of the needle may be open, however the user may nonetheless remove the biopsy needle assembly. At step 504, after determining that the biopsy needle assembly 52 has been removed, the computer system 18 displays an option on the biopsy control panel 20 for the user to either reinstall the currently installed biopsy needle assembly 52 or replace the currently installed biopsy needle assembly 52 with a new (second) biopsy needle assembly 52. The computer system 18 may display the option on the biopsy control panel 20 as a message screen 420, as depicted in FIG. 11. The message screen 420 may include a removal instruction 422 instructing the user to remove the biopsy needle assembly 52 from the patient, in case the needle is still in the patient. The message screen 420 includes a message 424 to either re-install the removed biopsy needle assembly 52, or to select a "replace needle selection" to replace the biopsy needle assembly 52 with a new biopsy needle assembly 52. For example, the "replace needle selection" may be a button displayed on the message screen 420 which the user can select using the biopsy control panel 20. Accordingly, the option to re-install the removed biopsy needle assembly 52 is the default option, and the user does not have to prompt the system or provide any input to the system to re-install the removed biopsy needle assembly 52. The option is given to the user so that the user can determine based on the point in the biopsy procedure, whether it is the best scenario to reinstall or replace the biopsy needle assembly 52. For example, the biopsy procedure may be completed, and aspirate mode is being used to clear out the aperture of the biopsy needle assembly 52. In which case, the user may choose to reinstall the currently installed biopsy needle assembly 52 and finish clearing the aperture.

Alternatively, the computer system 18 may be configured to require the user to select an option to re-install the removed biopsy needle assembly 52, in which case the message screen 420 includes a "re-install needle selection," such as a button displayed on the message screen 420 which the user can select using the biopsy control panel 20.

As described above, in some configurations of the biopsy needle assembly 52, outer cannula 84 comprises a separate introducer portion 89. In such case, the computer system 18 may be configured to only display the message screen 420 and to perform the process 400 when the computer system 18 detects that both the introducer portion 89 and the remainder of the biopsy needle assembly 52 have been removed.

At step 506, if the user does not select the "replace needle selection," the computer system 18 leaves the first drive member 65 and second drive member 74 in their respective positions when the biopsy needle assembly 52 was removed. At step 508, the biopsy needle assembly 52 is reinstalled on the motorized driver 52. Because the first and second needle interfaces 68, 76 and the first and second drive members 65, 74 were not moved between removing and reinstalling the biopsy needle assembly 52, the first and second needle interfaces 68, 76 and the respective first and second drive members 65, 74 remain properly aligned. In another example, the user may be in the beginning of a biopsy procedure and believes that the biopsy needle assembly 52 is not operating correctly. The user may instead choose to replace the currently installed biopsy needle assembly 52 and restart the procedure. Optionally, at step 510, the biopsy system 10 may enter the Setup mode, as described above, in order to confirm the saline flow, and a test cutting cycle can also performed. At step 512, the biopsy system 10 may enter the Test mode to verify proper operation of the biopsy system 10 before a biopsy is completed. The biopsy system 10 is now ready to proceed with a biopsy procedure.

For the option to install a new needle assembly of method 500, at step 514, the computer system 18 receives a selection by the user of the "replace needle assembly" selection, indicating selection of the option to replace the biopsy needle assembly 52 with second biopsy needle assembly 52. At step 516, the biopsy system 10 enters the Setup mode. At step 518, the computer system 18 may provide an audio signal that warns the user that the biopsy system 10 is about to operate the biopsy device 32, same or similar to the audio signal at step 203, described above. At step 520, the computer system 18 performs the driver homing as described in steps 204 and 206 above. At step 522, the second biopsy needle assembly 52 is installed on the motorized driver 50.

Figure 10:
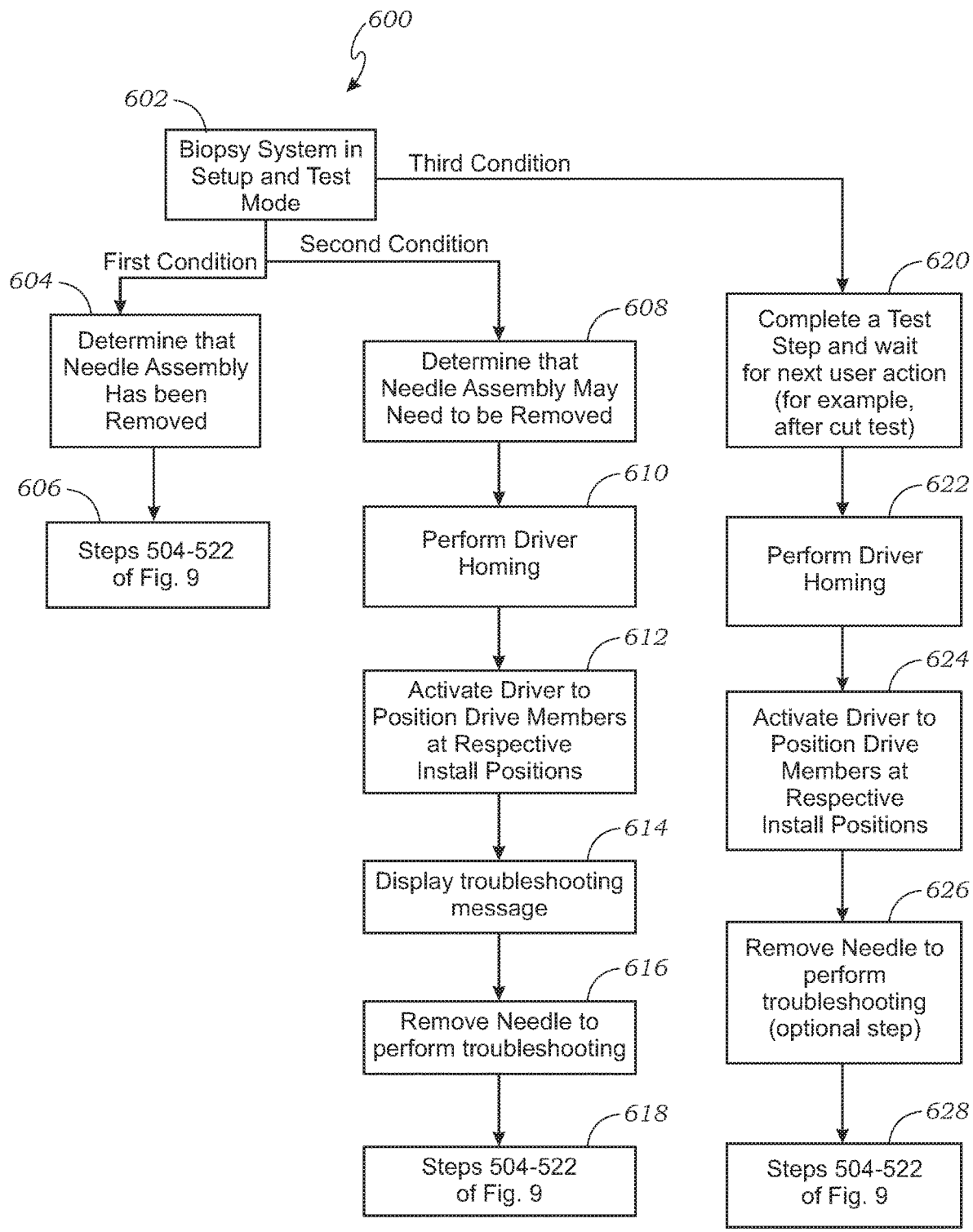
FIG. 10 illustrates a flow chart of a method for using the automated biopsy system of FIG. 1, according to another embodiment.

Turning to FIG. 10, in a fourth homing mode, the homing process 600 comprises a step 602 in which the biopsy system 10 is in the Setup and Test mode. As described above, in the Setup and Test mode, the computer system 18 runs the biopsy system 10 through various setup processes to prepare the biopsy system 10 to perform a biopsy procedure, and test processes to ensure that the biopsy system 10 is setup and functioning properly, including actuating the first and second drive members 65, 74. As some non-limiting examples, the Setup and Test procedure may include: determining that a biopsy needle assembly 52 is installed on the motorized driver 50; activating the motorized driver 50 by activating the motor 62 to move the first and second drive members 65, 74; test arming and firing the biopsy needle assembly 52; testing the lavage and aspiration functions of the biopsy system 10; etc. The test may fail for any number of conditions, such as for example, a leak in the biopsy system 10, a lack of proper vacuum level, no saline flow as selected by the user, cut test fail, as indicated by the user.

If any of the tests fail as detected by the computer system 18 or as indicated by the user via the biopsy control panel 20, the aperture on the currently installed biopsy needle assembly 52 may be closed by the computer system 18. This is contrary to typical operation, as many of the tests are conducted with an open aperture. Closing the aperture upon a failure is a non-obvious step to ensure alignment with the biopsy needle assembly 52 which may be reinstalled or replaced. This feature addresses the majority of the problems found during Usability Studies conducted during the development of the biopsy system 10, as users' typical instinct is to remove the biopsy needle assembly 52 if a test is failed thereby causing misalignment.

The homing process 600 in the fourth homing mode has three different options each applicable to a particular condition occurring during the Setup and Test mode. In a first condition, the biopsy system 10 determines that the biopsy needle assembly 52 has been removed from the driver 50 during the Setup and Test mode. This is a situation where the user removes the biopsy needle assembly 52 without the biopsy system 10 determining that the needle assembly 52 needs to be removed. In a second condition, the biopsy system 10 determines that the biopsy needle assembly 52 needs to be removed, such as due to detecting a failure during the Setup and Test mode. In a third condition, the biopsy system 10 completes a Test step and pauses to wait for the user to perform a next action. For instance, the Test mode may perform a cut test, as described above, and then the biopsy system 10 pauses for the user to proceed with the next Test step.

Still referring to FIG. 10, in the first condition of the homing process 600, at step 604, during the setup and test mode, the computer system 18 determines that the biopsy needle assembly 52 has been removed from the driver 50 by the user, same or similar to step 306 described above. At step 606, the biopsy system 10 performs the same process as steps 504-522 as shown in FIG. 9, and described above.

In the second condition of homing process 600, at step 608, the computer system 18 determines that the needle assembly 52 may need to be removed. This may occur because the biopsy system 10 detects a failure during the Setup and Test mode, or for other reason. At steps 610 and 612, the computer system 18 performs the driver homing as described in steps 204 and 206 with the needle assembly 52 installed on the driver 50. At step 614, the computer system 18 displays a troubleshooting message screen on the biopsy control panel 20 advising the user of troubleshooting steps to perform to correct the failure. The troubleshooting steps include an instruction to remover the needle assembly 52. At step 616, the needle assembly 52 is removed from the driver 50. At step 618 the biopsy system 10 performs the same process as steps 504-522 as shown in FIG. 9, and described above.

In the third condition of homing process 600, at step 620, the biopsy system 10 completes a Test step and pauses for the next user action. At steps 622 and 624, the computer system 18 performs the driver homing as described in steps 204 and 206 with the needle assembly 52 installed on the driver 50. Optionally, at step 626, the needle assembly 52 is removed from the driver 50 to perform troubleshooting. At step 628, the biopsy system 10 performs the same process as steps 504-522 as shown in FIG. 9, and described above.

Although particular embodiments have been shown and described, it is to be understood that the above description is not intended to limit the scope of these embodiments. While embodiments and variations of the many aspects of the disclosed inventions have been disclosed and described herein, such disclosure is provided for purposes of explanation and illustration only. Thus, various changes and modifications may be made without departing from the scope of the claims. For example, not all of the components described in the embodiments are necessary, and various embodiments may include any suitable combinations of the described components, and the general shapes and relative sizes of the components of the invention may be modified. While the systems and methods have been described cytological samples, they can be configured and utilized with any types of samples. Accordingly, embodiments are intended to exemplify alternatives, modifications, and equivalents that may fall within the scope of the claims. The disclosed inventions, therefore, should not be limited, except to the following claims, and their equivalents.

What is claimed is:

1. An automated biopsy system, comprising:
   a motorized driver having a first drive member configured to be operatively coupled with a first needle interface of a biopsy needle assembly removably installed on the motorized driver, wherein the motorized driver is configured to actuate the first drive member to thereby actuate the biopsy needle assembly via the first needle interface; and
   a controller operatively coupled to, and configured to control operation of, the motorized driver, wherein the controller is configured to perform a homing process, the homing process comprising
      determining a system test failure or a needle removal condition in which a first biopsy needle assembly installed on the motorized driver has been or should be removed from the motorized driver; and
      after determining the system test failure or needle removal condition, performing a driver homing comprising operating the motorized driver to position the first drive member in a first drive member home position for receiving a second biopsy needle assembly to be installed on the motorized driver.

2. The biopsy system of claim 1 wherein the second biopsy needle assembly includes a pre-set first needle interface in a first needle interface home position for operatively coupling with the first drive member when the first drive member is in the first drive member home position.

3. The biopsy system of claim 1, wherein the controller is configured to perform the driver homing prior to removal of the first biopsy needle assembly from the motorized driver.

4. The biopsy system of claim 1, wherein the controller is configured to perform the driver homing after detecting that the first biopsy needle assembly has been removed from the motorized driver.

5. The biopsy system of claim 1, wherein the controller is configured to perform the homing process for each of a plurality of homing modes.

6. The biopsy system of claim 5, the plurality of homing modes including a homing mode in which the homing process comprises
  detecting that the biopsy system has been powered ON from a powered OFF state with the first biopsy needle assembly installed on the motorized driver,
  displaying a message on a user interface display operatively coupled with the controller to remove the first biopsy needle assembly from the motorized driver,
  detecting that the first biopsy needle assembly has been removed from the motorized driver, and
  after detecting that the first biopsy needle assembly has been removed from the motorized driver, performing the driver homing.

7. The biopsy system of claim 5, the plurality of homing modes including a homing mode in which the homing process comprises
  verifying that the biopsy system has entered a standby mode after a biopsy procedure has been performed using the first biopsy needle assembly installed on the motorized driver,
  detecting that the first biopsy needle assembly has been removed from the motorized driver, and
  after detecting that the first biopsy needle assembly has been removed, performing the driver homing.

8. The biopsy system of claim 5, the plurality of homing modes including a homing mode in which the homing process comprises
  detecting, during one of a biopsy, lavage, or aspirate mode, that the first biopsy needle assembly has been removed from the motorized driver,
  after detecting that the first biopsy needle assembly has been removed, prompting a user to select, through the user interface, whether to install a second biopsy needle assembly, or reinstall the first biopsy needle assembly,
  upon receiving a user selection to install the second biopsy needle assembly, performing the driver homing; and
  upon receiving a user selection to reinstall the first biopsy needle assembly, leaving the first drive member in a same position as when the first biopsy needle was removed.

9. The biopsy system of claim 5, the plurality of homing modes including a homing mode in which homing process comprises
  determining, during a setup and test procedure of the biopsy system, that a test fail condition has been met, and
  after determining that the test fail condition has been met, performing the driver homing while the first biopsy needle assembly remains installed on the motorized driver.

10. The biopsy system of claim 1, wherein the driver homing further comprises actuating the motorized driver to actuate the biopsy needle assembly to close a specimen cutting and receiving aperture on a distal end of the first biopsy needle assembly.

11. The biopsy system of claim 1,
  wherein the motorized driver further comprises a second drive member configured to operatively couple with a second needle interface of the first biopsy needle assembly, wherein the motorized driver is configured to actuate the second drive member thereby actuating the biopsy needle assembly via the second needle interface, and
  wherein the homing process further comprises operating the motorized driver to position the second drive member in a second drive member home position for receiving the first biopsy needle assembly to be installed on the motorized driver.

12. An automated biopsy system, comprising:
  a motorized driver having a first drive member for actuating a first biopsy needle assembly removably installed on the motorized driver, the first drive member configured to operatively couple with a first needle interface of a biopsy needle assembly removably installed on the motorized driver, the motorized driver configured to actuate the first drive member to thereby actuate the first biopsy needle assembly via the first needle interface;
  a user interface having a display and a user input device configured to receive user commands;
  a controller operatively coupled with each of the motorized driver and user interface, wherein the controller is configured to control operation of the motorized driver including performing a homing process comprising
    determining a system test failure or a needle removal condition in which the first biopsy needle assembly installed on the motorized driver either has been or should be removed from the motorized driver and reinstalled or replaced with a second biopsy needle assembly,
    after determining the system test failure or needle removal condition, displaying a message on the user interface display prompting a user to select, through the user interface, whether to install a second biopsy needle assembly or reinstall the first biopsy needle assembly,
    upon receiving a user selection to install the second biopsy needle assembly, performing a driver homing comprising operating the motorized driver to position the first drive member in a first drive member home position for receiving the second biopsy needle assembly, wherein the second biopsy needle assembly is configured to be installed on the motorized driver with the first needle interface in the first needle home position, and
    upon receiving a user selection to reinstall the first biopsy needle assembly, leaving the first drive member in a same position as when the first biopsy needle was removed.

13. The biopsy system of claim 12,
  wherein the motorized driver further comprises a second drive member configured to operatively couple with a second needle interface of the first biopsy needle assembly, and the motorized driver is configured to actuate the second drive member thereby actuating the biopsy needle assembly via the second needle interface, and
  wherein the homing process further comprises
  upon receiving the user selection to install the second biopsy needle assembly, as a part of the driver homing, operating the motorized driver to position the second drive member in a second drive member home position for receiving the second biopsy needle assembly, wherein the second biopsy needle assembly is configured to be installed on the motorized driver with the second needle interface in the second needle home position, and upon receiving the user selection to reinstall the first biopsy needle assembly, leaving the second drive member in a same position as when the first biopsy needle assembly was removed.

14. The biopsy system of claim 12, wherein the controller is configured to perform the driver homing prior to removal of the first biopsy needle assembly from the motorized driver.

15. The biopsy system of claim 12, wherein the controller is configured to perform the driver homing after detecting that the first biopsy needle assembly has been removed from the motorized driver.

16. An automated biopsy system, comprising:
a motorized driver configured to have a biopsy needle assembly removably installed thereon, and
a controller operatively coupled with the motorized driver, wherein the controller is configured to
determine a system test failure or a needle removal condition in which a first biopsy needle assembly installed on the motorized driver has been or should be removed from the motorized driver, and
after determining the system test failure or needle removal condition, perform a driver homing comprising operating the motorized driver to position a first drive member of the motorized driver at a first drive member home position for receiving a second biopsy needle assembly to be removably installed on the motorized driver.

17. The system of claim 16, wherein the second biopsy needle assembly includes a first needle interface configured for operatively coupling with the first drive member when the first drive member is in the first drive member home position.

18. The system of claim 16, wherein the controller is configured to perform the driver homing prior to removal of the first biopsy needle assembly from the motorized driver.

19. The system of claim 16, wherein the controller is configured to perform the driver homing after detecting that first the biopsy needle assembly has been removed from the motorized driver.

20. The system of claim 16,
wherein the motorized driver comprises a second drive member configured to operatively couple with a second needle interface of a biopsy needle assembly installed on the motorized driver, and
wherein, as a part of the homing process, the controller is configured to operate the motorized driver to position the second drive member in a second drive member home position for receiving the second needle interface in a second needle home position when the second biopsy needle assembly is installed on the motorized driver.

* * * * *